(12) United States Patent
Baccelli et al.

(10) Patent No.: US 8,870,870 B2
(45) Date of Patent: *Oct. 28, 2014

(54) VERTEBRAL FIXING SYSTEM

(75) Inventors: Christian Baccelli, Saucats (FR); Karl P. Belliard, La Membrolle sur Longuenee (FR); Keyvan Mazda, Paris (FR)

(73) Assignee: Zimmer Spine S.A.S., Bordeaux (FR)

( * ) Notice: Subject to any disclaimer, the term of this patent is extended or adjusted under 35 U.S.C. 154(b) by 291 days.

This patent is subject to a terminal disclaimer.

(21) Appl. No.: 13/248,453

(22) Filed: Sep. 29, 2011

(65) Prior Publication Data

US 2012/0022591 A1 Jan. 26, 2012

Related U.S. Application Data

(63) Continuation of application No. 12/375,265, filed as application No. PCT/FR2006/050898 on Sep. 18, 2006, now Pat. No. 8,172,843.

(30) Foreign Application Priority Data

Sep. 20, 2005 (FR) ..................................... 05 09570
Feb. 22, 2006 (FR) ..................................... 06 50609

(51) Int. Cl.
*A61B 17/82* (2006.01)
*A61B 17/70* (2006.01)

(52) U.S. Cl.
CPC ......... *A61B 17/7053* (2013.01); *A61B 17/7032* (2013.01); *A61B 17/707* (2013.01); *A61B 17/7041* (2013.01)
USPC .............................. 606/74; 606/324; 606/263

(58) Field of Classification Search
USPC ........... 606/103, 139, 232, 247–279, 60, 246, 606/74, 324; 623/13.14; 24/132 R, 312 AA, 24/132 WL
See application file for complete search history.

(56) References Cited

U.S. PATENT DOCUMENTS 902,040 A 10/1908 Wyckoff
1,346,940 A 7/1920 Collins
(Continued)

FOREIGN PATENT DOCUMENTS

DE 19716504 12/1998
EP 0780096 6/1997
(Continued)

OTHER PUBLICATIONS

Notice of Allowance issued in U.S. Appl. No. 11/877,160, mailed Oct. 31, 2011, 7 pages.
(Continued)

*Primary Examiner* — Pedro Philogene
*Assistant Examiner* — Lynnsy Summitt
(74) *Attorney, Agent, or Firm* — Seager, Tufte & Wickhem, LLC

(57) ABSTRACT

A vertebral fixing system comprising a connecting part with two longitudinal elements coupled to each other at a first end and having mutually facing recesses for receiving a rod. A portion of a flexible ligature extends through orifices of the two longitudinal elements to define a loop opposite two free ends of the flexible ligature. The two longitudinal elements are engaged at a second end of the connecting part via a locking means. When the two longitudinal elements of the connecting part are locked at the second end of the connecting part, two strands of the flexible ligature are pinched between the rod and a wall of the mutually facing recesses of the two longitudinal elements of the connecting part, preventing the flexible ligature from moving in translation relative to the connecting part.

20 Claims, 5 Drawing Sheets

(56) References Cited

U.S. PATENT DOCUMENTS

| | | | |
|---|---|---|---|
| 2,049,361 A | 7/1936 | Johan | |
| 4,570,618 A | 2/1986 | Wu | |
| 5,030,220 A | 7/1991 | Howland | |
| 5,304,178 A | 4/1994 | Stahurski | |
| 5,356,412 A | 10/1994 | Golds et al. | |
| 5,413,576 A | 5/1995 | Rivard | |
| 5,449,361 A | 9/1995 | Preissman | |
| 5,609,634 A | 3/1997 | Voydeville | |
| 5,667,508 A | 9/1997 | Errico | |
| 5,669,917 A | 9/1997 | Sauer et al. | |
| 5,702,399 A * | 12/1997 | Kilpela et al. | 606/308 |
| 5,720,751 A | 2/1998 | Jackson | |
| 5,772,663 A | 6/1998 | Whiteside et al. | |
| RE36,221 E | 6/1999 | Breard et al. | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,179,838 B1 | 1/2001 | Fiz | |
| 6,228,096 B1 | 5/2001 | Marchand | |
| 6,241,740 B1 | 6/2001 | Davis et al. | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,352,557 B1 | 3/2002 | Ferree | |
| 6,391,030 B1 | 5/2002 | Wagner et al. | |
| 6,419,702 B1 | 7/2002 | Ferree | |
| 6,447,518 B1 | 9/2002 | Krause et al. | |
| 6,478,798 B1 | 11/2002 | Howland | |
| 6,514,255 B1 * | 2/2003 | Ferree | 606/263 |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,605,091 B1 | 8/2003 | Iwanski | |
| 6,616,669 B2 | 9/2003 | Ogilvie et al. | |
| 6,656,179 B1 | 12/2003 | Schaefer et al. | |
| 6,656,185 B2 | 12/2003 | Gleason et al. | |
| 6,682,533 B1 | 1/2004 | Dinsdale et al. | |
| 6,689,140 B2 | 2/2004 | Cohen | |
| 6,695,852 B2 | 2/2004 | Gleason | |
| 6,723,335 B1 | 4/2004 | Moehlenbruck et al. | |
| 6,746,452 B2 | 6/2004 | Tuke et al. | |
| 6,773,438 B1 | 8/2004 | Knodel et al. | |
| 6,946,000 B2 | 9/2005 | Senegas et al. | |
| 7,481,828 B2 | 1/2009 | Mazda et al. | |
| 7,699,874 B2 | 4/2010 | Young | |
| 7,959,654 B2 | 6/2011 | Mazda et al. | |
| 2002/0116013 A1 | 8/2002 | Gleason et al. | |
| 2002/0198538 A1 | 12/2002 | Kortenbach et al. | |
| 2004/0087979 A1 | 5/2004 | Field et al. | |
| 2004/0097942 A1 | 5/2004 | Allen et al. | |
| 2004/0138666 A1 | 7/2004 | Molz, IV et al. | |
| 2005/0070958 A1 | 3/2005 | Swayze et al. | |
| 2005/0085815 A1 | 4/2005 | Harms | |
| 2005/0131404 A1 | 6/2005 | Mazda | |
| 2005/0154403 A1 | 7/2005 | Sauer et al. | |
| 2005/0228375 A1 * | 10/2005 | Mazda et al. | 606/61 |
| 2005/0273983 A1 | 12/2005 | Mattchen | |
| 2006/0235387 A1 | 10/2006 | Peterman | |
| 2006/0235391 A1 | 10/2006 | Sutterlin | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda | |
| 2009/0138048 A1 | 5/2009 | Baccelli et al. | |

FOREIGN PATENT DOCUMENTS

| | | |
|---|---|---|
| EP | 1815812 | 8/2007 |
| FR | 522040 | 7/1921 |
| FR | 26156 | 9/1923 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| FR | 2897771 A1 | 8/2007 |
| GB | 2269753 | 2/2004 |
| JP | 2001299770 | 10/2001 |
| WO | WO9416635 A1 | 8/1994 |
| WO | 0154599 | 8/2001 |
| WO | WO027621 A1 | 1/2002 |
| WO | WO027622 A1 | 1/2002 |
| WO | 0209604 A1 | 2/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | WO 2004010881 A1 * | 2/2004 |
| WO | WO2004010881 A1 | 2/2004 |
| WO | WO 2005020860 A3 | 3/2005 |
| WO | WO2005120277 A1 | 12/2005 |
| WO | WO2006034423 A2 | 3/2006 |
| WO | WO 2006106268 A3 | 10/2006 |
| WO | WO 2006106246 | 12/2006 |
| WO | WO 2007023240 A3 | 3/2007 |
| WO | WO2007034112 A1 | 3/2007 |
| WO | WO 2007036657 | 4/2007 |
| WO | WO2007099258 A2 | 9/2007 |

OTHER PUBLICATIONS

Notice of Allowance issued in U.S. Appl. No. 11/996,918, mailed Dec. 19, 2011, 9 pages.
English Translation of International Preliminary Report issued in International Patent Application No. PCT/FR2006/050898 on Patentability Chapter I dated Apr. 29, 2008, 6 pages.
English Translation of International Preliminary Report on Patentability Chapter I issued in International Patent Application No. PCT/FR2006/ 050909 dated Apr. 8, 2008, 5 pages.
English Translation of the Written Opinion of the International Search Authority issued in International Patent Application No. PCT/FR2006/ 050909 dated Apr. 2, 2008, 4 pages.
English Translation of the Written Opinion of the International Search Authority issued in International Patent Application No. PCT/FR2006/050898 dated Apr. 28, 2008, 5 pages.
European Search Report issued in European Patent Application No. EP 08305183 dated Mar. 19, 2009, 10 pages.
European Search Report issued in European Patent Application No. EP 08305326 dated Nov. 12, 2008, 3 pages.
European Search Report issued in European Patent Application No. EP 2052689 dated Apr. 15, 2008, 6 pages.
European Search Report issued in European Patent Application No. EP08305326 on Nov. 18, 2006, 3 pages.
French Preliminary Search Report and Written Opinion in French Patent Application No. FR200650609 dated Jun. 30, 2006, 5 pages.
International Search Report issued in International Patent Application No. WO2009053423 dated May 19, 2009, 4 pages.
International Search Report issued in International Patent Application No. PCT/EP2008/063682, mailed Nov. 24, 2008 3 pages.
International Search Report Issued in International Patent Application No. PCT/FR2006/050909, published as WO/2007/034112, dated Jan. 24, 2007, 3 pages.
Office Action issued in U.S. Appl. No. 10/521,914 mailed Dec. 29, 2006, 21 pages.
Office Action issued in U.S. Appl. No. 10/521,914 mailed Mar. 19, 2008, 7 pages.

(56) References Cited

OTHER PUBLICATIONS

Office Action issued in U.S. Appl. No. 10/521,914 mailed Jun. 16, 2006, 13 pages.
Office Action issued in U.S. Appl. No. 10/521,914 mailed Jul. 30, 2007, 13 pages.
International Search Report and Written Opinion issued in International Patent Application No. PCT/US2009/038977 mailed Jul. 22, 2009, 13 pages.
Korean Examination report issued in Korean Patent Application No. 1020057001238 mailed Feb. 23, 2010, 3 pages.
French Preliminary Search Report issued in French Patent Application No. FR0209317 dated Apr. 9, 2003, 1 page.
French Preliminary Search Report issued in French Patent Application No. FR0509629 mailed Jun. 9, 2006, 2 pages.
International Search Report issued in International Patent Application No. PCT/FR2003/02307 dated Jan. 2, 2004, 2 pages.
Australian Search Report issued in Australian Patent Application No. 2003267529 dated Nov. 15, 2007, 2 pages.
French Preliminary Search Report issued in French Patent Application No. FR0509570 dated Jun. 29, 2006, 2 pages.
International Search Report issued in International Patent Application No. PCT/FR2006/050898 dated Feb. 2, 2007, 2 pages.
Written Opinion issued in International Patent Application No. PCT/US2009/038977 mailed Feb. 24, 2010, 7 pages.
European Search Report issued in European Patent Application No. 07 301 454.0, mailed Sep. 25, 2008, 8 pages.
Partial European Search Report issued in European Patent Application No. 07 301 483.9, completed Apr. 15, 2008, mailed Apr. 23, 2008, 6 pages.
European Search Report and Search Opinion issued in European Patent Application No. 07 301 483.9, completed Apr. 15, 2008, mailed Jul. 10, 2008, 10 pages.
International Search Report and Written Opinion issued in International Patent Application No. PCT/EP2008/064344, completed Jan. 16, 2009, mailed May 19, 2009, 11 pages.
International Search Report and Written Opinion issued in International Patent Application No. PCT/EP2008/062791, completed Nov. 18, 2008, mailed Dec. 4, 2008, 10 pages.
French Preliminary Search Report issued in French Patent Application No. 0757814, issued May 22, 2008, 2 pages.
International Preliminary Report on Patentability issued in International Patent Application No. PCT/EP2008/062791, Mar. 30, 2010, 7 pages
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 12 pages.
French Preliminary Search Report issued in French Patent Application No. FR 0405611, dated Jan. 12, 2005, 2 pages.
International Search Report issued in International Patent Application No. PCT/FR2005/001280, Nov. 7, 2005, 3 pages.
Written Opinion issued in International Patent Application No. PCT/FR2005/001280, Nov. 25, 2006, 5 pages.
International Search Report issued in International Patent Application No. PCT/EP2008/064344, published as WO/2008/053423, mailed May 19, 2009, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 11/877,160, mailed Nov. 26, 2010, 10 pages.
Office Action issued in U.S. Appl. No. 11/996,918, mailed Feb. 14, 2011, 12 pages.
Office Action issued in U.S. Appl. No. 12/059,634, mailed Feb. 15, 2011, 15 pages.
Office Action issued in U.S. Appl. No. 12/408,592, mailed Feb. 18, 2011, 17 pages.
Notice of Allowance issued in U.S. Appl. No. 12/358,748, mailed Feb. 23, 2011, 5 pages.
Office Action issued in U.S. Appl. No. 11/877,160, mailed Apr. 12, 2011, 12 pages.
Office Action issued in U.S. Appl. No. 12/059,634, mailed Jun. 22, 2011, 15 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 12/375,265, mailed Aug. 25, 2011, 10 pages.
Office Action issued in U.S. Appl. No. 12/408,592, mailed Sep. 22, 2011, 24 pages.
Office Action issued in U.S. Appl. No. 12/059,634, mailed Oct. 5, 2011, 12 pages.

\* cited by examiner

VERTEBRAL FIXING SYSTEM

CROSS-REFERENCE TO RELATED APPLICATIONS

This application is a continuation of U.S. patent application Ser. No. 12/375,265, filed on Mar. 9, 2009 now U.S. Pat. No. 8,172,843, which is a U.S. National Phase Entry of International Application No. PCT/FR2006/050898, filed Sep. 18, 2006, which claims priority to French Application Nos. FR 0650609, filed Feb. 22, 2006 and FR 0509570, filed Sep. 20, 2005, the entire disclosures of which are incorporated herein by reference.

TECHNICAL FIELD OF THE INVENTION

The present invention relates to vertebral fixing system suitable for being mounted on a vertebra.

An intended field of application is particularly, but not exclusively, the treatment of scoliosis, or more generally correcting abnormal curvatures of the spine.

BACKGROUND OF THE RELATED ART

The spine is constituted by superposed vertebrae that are normally in alignment along a vertical axis, going from the lumbar vertebrae to the cervical vertebrae, each vertebra presenting a posterior wall from which there projects a spinous process and two sides having walls from which there project the ribs and/or transverse processes. When the spine of an individual presents abnormal curvature, the vertebrae are inclined relative to one another and relative to said vertebral axis. The sides of the vertebrae situated on one side are thus moved closer together forming a concave side, whereas the sides of the vertebrae on the other side are spaced apart from one another and form a convex side.

In order to straighten the spinal column, the sides of the vertebrae on the concave side are spaced apart from one another and moved relative to one another to distances that are substantially equivalent to those between the sides of the vertebrae on the other side. In order to keep the vertebrae in that relative positioning, known devices have screws that are inserted in the vertebrae or hooks that are inserted along the inside wall of the vertebral canal, and rods that are for interconnecting the screws or the hooks.

The hooks are generally inserted in pairs into each vertebra and on either side close to the pedicles, with their heads projecting from the posterior wall of the vertebra, one on either side of the spinous process. By way of example, the heads form a socket suitable for receiving a rod that is held in place by means of a nut screwed onto the head so as to press against the rod. The rows constituted by the heads of the hooks situated on either side of the spinous processes are interconnected and held in a fixed position by two rods that are parallel to each other and to the axis of the spine.

Nevertheless, it is difficult to use such hooks since the operator must under no circumstances interfere with the spinal cord that extends along the center of the vertebral canal, since otherwise there is a danger of paralyzing the patient.

The use of screws makes it possible to diminish the risks of the operation. The screws likewise have socket-forming heads and they are inserted in pairs into the posterior walls of the vertebrae in the pedicles on either side of the spinous process. Thus, the screws constitute points for fixing the vertebrae so as to hold them relative to one another. Nevertheless, they are necessarily introduced into the pedicles of the vertebrae, and under certain circumstances such pedicles can be small in size or damaged.

The problem that arises and that the present invention seeks to solve is how to establish fixing points when it is not possible to introduce screws into the vertebrae in the curved portion of the spine and when the use of hooks is too dangerous. PCT patent application WO 2004/010881 in the name of the Applicant describes a vertebral fixing system that enables the problem to be solved.

That vertebral fixing system adapted to be mounted on a vertebra of the spine to connect it to a rod comprises:

a connecting part placed facing said rib and/or said transverse process and suitable for being connected to said rod;

an elongate flexible ligature suitable for connecting together said connecting part and at least one rib and/or one transverse process; and adjustable locking means fastened to said connecting part, said ligature having a first end secured to said connecting part and a free second end suitable for sliding in said connecting part to form a loop, said locking means being suitable for holding in a fixed position both said connecting part relative to said rod, and a length of said ligature between said ends that is suitable for being prevented from moving in translation relative to said connecting part by said adjustable locking means, whereby the loop presents a length that is determined so as to prevent relative displacement of said rod and said vertebra in opposite directions.

That system is satisfactory, but under certain circumstances it can present the following drawback. When the surgeon exerts traction on the free end of the flexible ligature, the ligature can be jammed by friction against the bottom face of the process. Under such circumstances, it will be understood that although the length of the ligature between the bottom face of the process and the zone where traction is applied to the ligature is indeed under tension, the length that extends between the end of the ligature that is secured to the elongate passageway and the bottom face of the process is not under tension. Thus, overall, the ligature does not perform its function of fastening to the vertebra in appropriate manner.

SUMMARY OF THE INVENTION

An object of the present invention is to provide a vertebral fixing system that enables the above-mentioned drawbacks to be avoided and that provides controlled locking of the ligature.

According to the invention, to achieve this object, the vertebral fixing system suitable for being mounted on a vertebra of the spine in order to connect it to a rod comprises:

a connecting part presenting first and second sides and suitable for being connected to said rod;

a flexible ligature of elongate shape suitable for connecting together said connecting part and at least one rib and/or transverse process and/or a portion of the posterior arc of a vertebra; and adjustable locking means mounted on said connecting part; and said system is characterized in that:

said ligature presents two free ends;

said connecting part defines at least one passageway for passing said ligature in such a manner that two distinct strands of said ligature can be engaged in said passageway(s) so that said two ligature strands define a first ligature portion forming a loop that extends from a first side of said connecting part, and second and third ligature portions extending from the other side of said connecting part between respective ones of said ligature strands and said free ends; and said locking means are distinct from the connecting part and co-operate therewith by screw-fastening, said locking means being capable of taking a first position relative to the connecting part in which the two ligature strands are free in said strand-passing passageway(s), a second position relative to the connecting part in which the two ligature strands are prevented from moving in translation relative to the connecting part, and intermediate positions in which a coefficient of friction is created between said ligature strands and said connecting part.

It will be understood that because the two ligature strands that are on either side of the transverse process are both placed in one or more passageways, when the locking means are brought into their locking position, both ligature strands can be used to exert the tension needed for fixing to the vertebra by means of a rib and/or a portion of the posterior arc of a vertebra and/or a transverse process.

In addition, since the locking means co-operate with the connecting part by screw-fastening, the "dimensions" of the passageways can be defined accurately during the various stages of clamping and then locking the ligature.

Preferably, the connecting part defines a single passageway and both ligature strands are engaged in the single passageway.

Also preferably, the single passageway is defined firstly by the outside surface of the portion of the rod that is engaged in the connecting part and secondly by a wall of the connecting part, and the locking means are suitable for modifying the section of the passageway.

When the locking means are in their second position, this ensures effective clamping of the two ligature strands, thereby preventing them from moving.

In a first embodiment, the connecting part comprises two longitudinal elements having first ends that are hinged together, each of said longitudinal elements presenting a recess suitable for receiving a portion of a section of said rod, a wall of said recess co-operating with the side surface of said rod to define said passageway for passing said ligature strands, said locking means being mounted at the two second ends of said longitudinal elements.

In a second embodiment, the connecting part comprises a part that is generally U-shaped, suitable for receiving said rod, and having the outer ends of the limbs of the U-shape threaded, and the adjustable locking means comprise a tapped ring suitable for co-operating with the thread on the U-shaped part, tightening the ring causing the limbs of the part to be clamped against the rod.

Preferably, said passageway(s) is/are constituted by the space between the inside wall of the recess formed in said connecting part and the side wall of said rod.

BRIEF DESCRIPTION OF THE DRAWINGS

Other characteristics and advantages of the invention appear better on reading the following description of embodiments of the invention given by way of non-limiting example. The description refers to the accompanying figures, in which.

DETAILED DESCRIPTION

Figure 1:
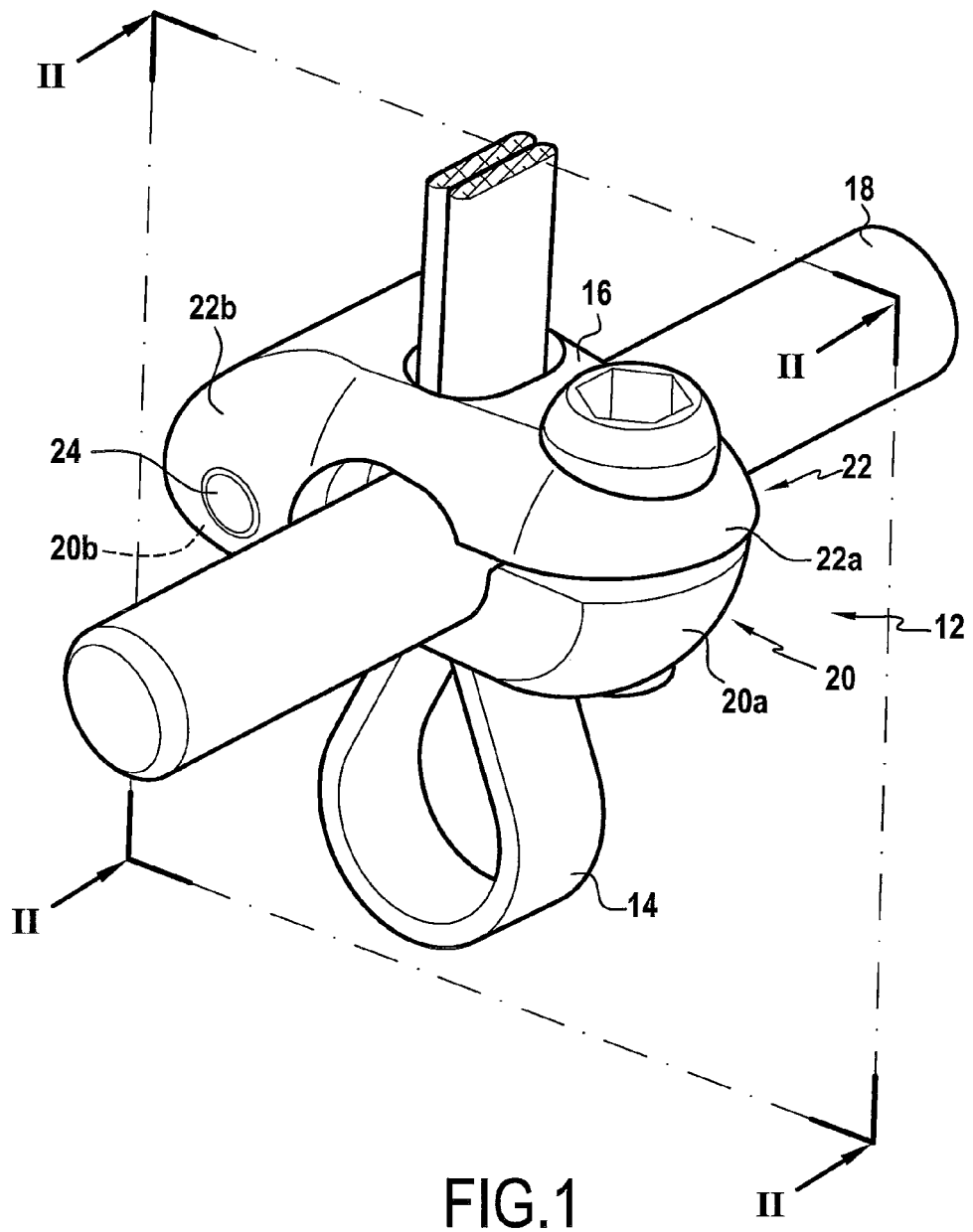
FIG. 1 is a perspective view of a first embodiment of a vertebral fixing system.

As shown in FIG. 1, in the first embodiment, the vertebral fixing system comprises a connecting part 12, a flexible ligature 14, and adjustable locking means 16. The flexible ligature 14 is of elongate shape and is capable of matching the outline of the parts it is to connect together. In this figure, there can also be seen the rod 18 that is to be secured to the vertebra by means of the vertebral fixing system. In the first embodiment, the connecting part 12 is constituted by two longitudinal elements given respective references 20 and 22, each having a first end 22a, 20a and a second end 22b, 20b.

Figure 2C:
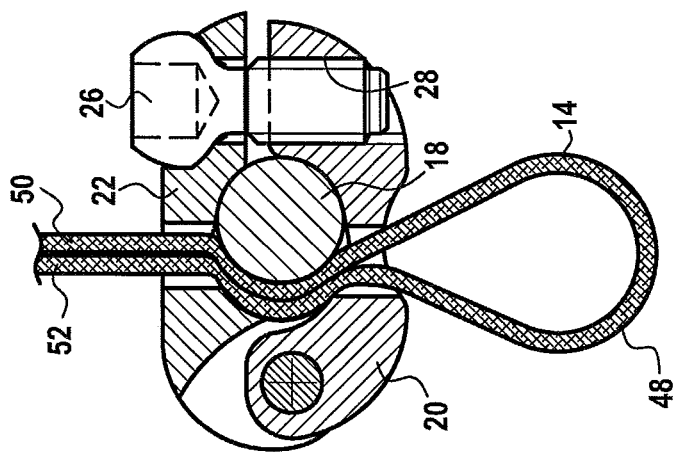
FIGS. 2A, 2B, and 2C are vertical section views of the fixing system showing the use of said system as shown in FIG. 1.
Figure 2B:
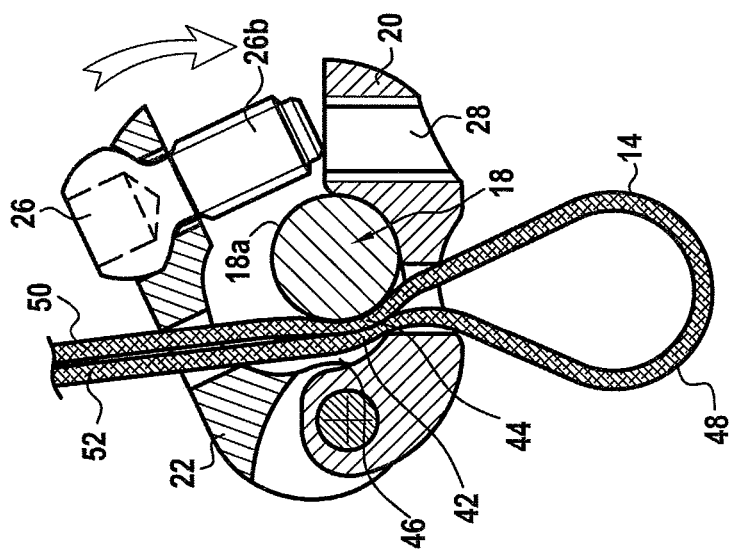
Figure 2A:
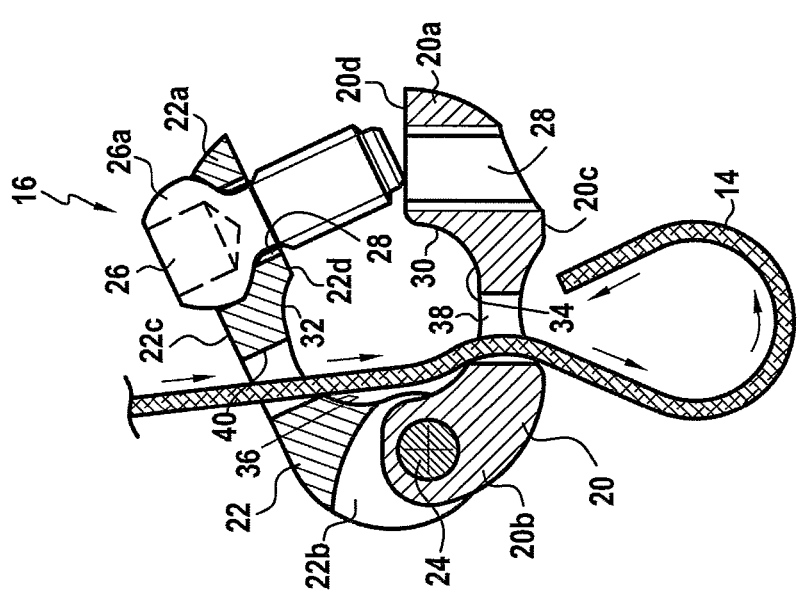

As can be seen better in FIG. 2A, the longitudinal elements 20 and 22 are hinged to each other at their second ends 20b, 22b about a pivot pin 24.

In the embodiment described, the locking means are constituted by a screw 26 having a head 26a that is engaged in a bore 28 formed in the first end 22a of the longitudinal element 22. The first end 20a of the longitudinal element 20 is pierced by a tapped bore 28 for co-operating with the threaded shank 26b of the screw 26. Each longitudinal element 20, 22 has an outside face 20c, 22c and an inside face 20d, 22d. The longitudinal elements 20 and 22 are mounted in such a manner that the inside faces 20d, 22d of the longitudinal elements face each other. The inside faces 20d, 22d of the longitudinal elements 20 and 22 have respective mutually-facing recesses 30 and 32, each of substantially semicylindrical shape. The recesses 30 and 32 define walls 34 and 36 which are ruled surfaces having generator lines parallel to the pivot axis 24. Finally, slots 38 and 40 cause the bottoms of the recesses 30 and 32 to communicate with the outside faces 20c and 22c of the longitudinal elements 20 and 22. As explained in greater detail below, the recesses 30 and 32 are for receiving the rod 18 together with a strand of the ligature 14, the slots 38 and 40 serving to pass the ligature 14.

With reference to FIGS. 2A to 2C, there follows an explanation of how the fixing system is used.

In FIG. 2A, there can be seen the longitudinal elements 20 and 22 in the spaced-apart position, a position in which the locking means 16 are naturally not active, the threaded shank 26b of the screw 26 not being engaged in the bore 28. The ligature 14 is engaged in the slots 38 and 40 of the longitudinal elements against one portion of the inside wall 34, 36 of the recesses 30 and 32. The rod 18 is then introduced into the recess 30 of the longitudinal element 20 so that the two strands 42 and 44 of the ligature 14 are disposed between the inside wall of the recesses 30 and 32 and the side face 18a of the rod 18. These two surfaces define a passageway 46 for passing the ligature 14 and having the strands 42 and 44 of the ligature 14 placed therein.

As shown better in FIG. 2B, the strands 42 and 44 of the ligature define a portion of the ligature 14 that forms a loop 48 that extends beyond the outside face 20c of the longitudinal element 20, and also two free portions 50 and 52 that extend beyond the outside face 22c of the longitudinal element 22. When the longitudinal elements 20 and 22 are spaced apart as shown in FIG. 2B, the ligature 14 can slide freely along the passageway 46. Once the portion 48 of the ligature 14 forming the loop is placed around the transverse process or a rib or indeed a portion of the posterior arc of a vertebra, the surgeon engages the threaded shank 26b of the screw 26 in the tapped bore 28, causing the longitudinal element 22 to come progressively closer to the longitudinal element 20. This approach simultaneously reduces the section of the passageway 46 in which the strands 42 and 44 of the ligature are engaged and simultaneously introduces a certain coefficient of friction between the ligature and respectively the rod 18 and the walls of the recesses 30 and 32. Nevertheless, it is still possible for the surgeon to extract traction on the free ends 50 and 52 of the ligature 14 until sufficient tension is obtained in the ligature around the vertebral process. Once the tension in the ligature is sufficient for providing appropriate fastening, the surgeon finishes off tightening the screw 26 in the tapped bore 28, thus locking the longitudinal elements 20 and 22 together. Simultaneously, it will readily be understood that the strands 42 and 44 of the ligature are pinched between the rod 18 and the wall of the recesses 30 and 32.

In this locking position, the rod 18 is thus secured to the ligature 14 via the connecting part 12.

It will also be understood that because the surgeon exerts traction only on the free ends 50 and 52 of the ligature 14, there is no risk of jamming between the ligature 14 and the bottom face of the transverse process or of the rib, thus guaranteeing that effective fastening is provided with the transverse process or the rib or indeed a portion of the posterior arc of a vertebra.

Figure 3:
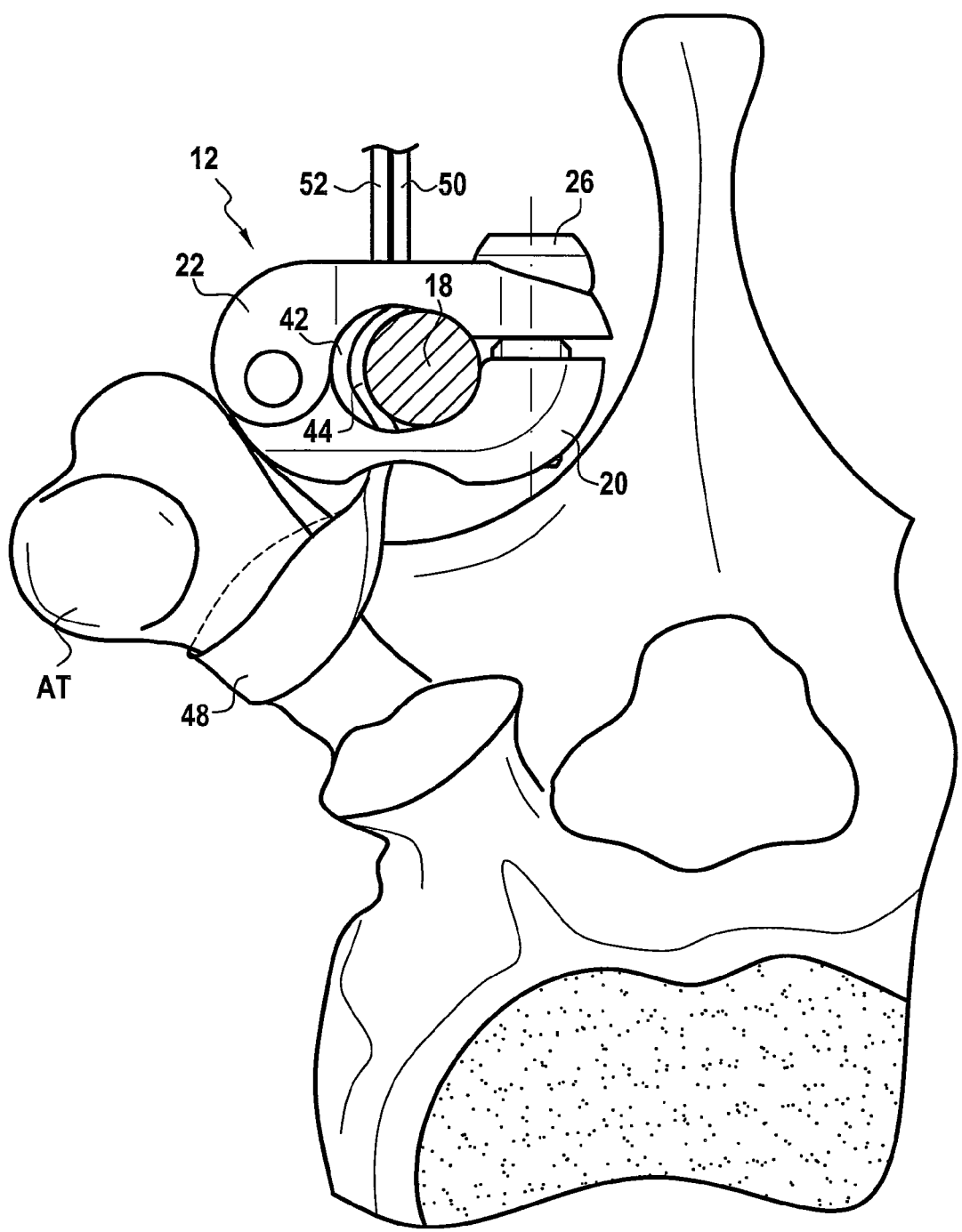
FIG. 3 is a face view showing the FIG. 1 fixing system put into place on a vertebra.
Figure 4:
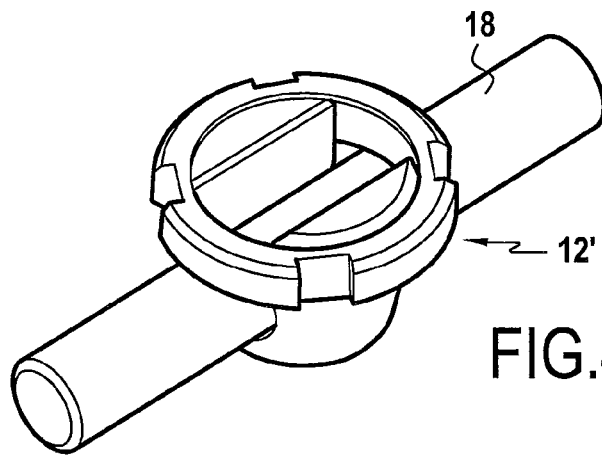
FIG. 4 is a perspective view of a second embodiment of the fixing system, the ligature not being shown.
Figure 5:
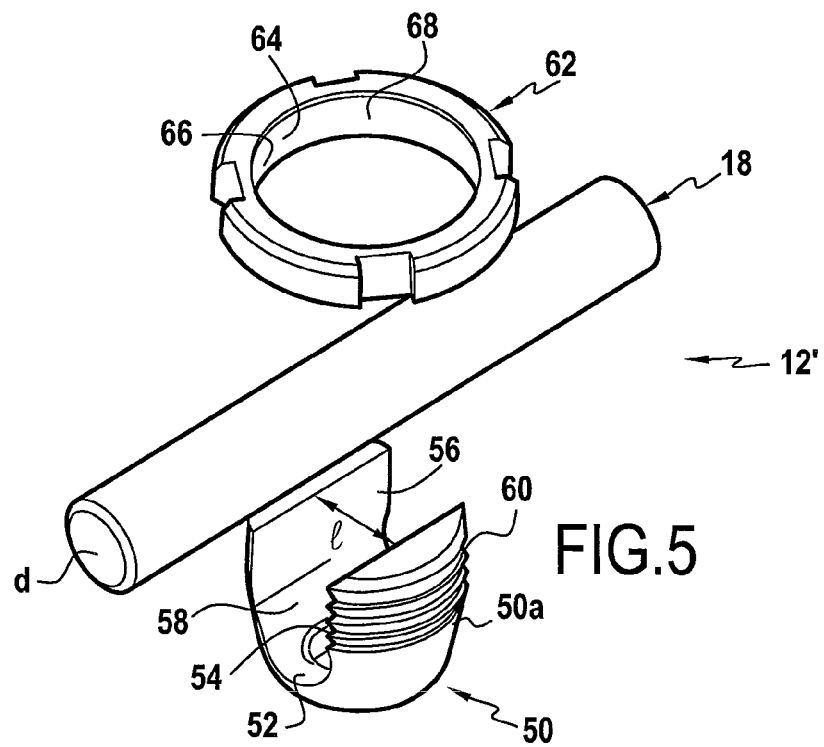
FIG. 5 is an exploded view of the connection device of FIG. 4.

This is shown in FIG. 3, where reference AT identifies the transverse process.

In the above description, both of the strands 42 and 44 of the ligature are disposed in the recesses 30 and 32 on the same side of the rod 18. This disposition serves to obtain an optimum result. Nevertheless, it would not go beyond the invention if the strands 42 and 44 of the ligature 14 were to be placed on opposite sides of the rod 18. Under such circumstances, it should be considered that the outside face 18a of the rod 18 and the inside walls of the recesses 30 and 32 define two passageways, respectively for passing each of the strands 42 and 44 of the ligature 14.

FIGS. 4 to 7B show a second embodiment of the fixing system.

In these figures, there can be seen the rod 18, the connecting part now referenced 12', and the flexible ligature 14.

In this embodiment, the connecting part 12' is constituted by a part 50 that is generally U-shaped. The inside wall of this part is constituted by a bottom 52 of substantially semicylindrical shape and by two substantially plane portions 54 and 56 that correspond to the two limbs of the part 50. The width l of the recess 58 formed in the part 50 is substantially equal to the diameter d of the rod 18. On its outside face 50a which is circularly symmetrical about a longitudinal axis of the part 50, there is provided a thread 60 occupying its upper portion. The thread 60 is located entirely above the rod 18 when it is put into place in the recess 58. The thread 60 is designed to co-operate with a clamping ring 62 that constitutes the adjustable locking means. This ring has a slightly frustoconical bore 64 with an inside face 66 that carries tapping 68.

It can thus be understood that when the ring 62 is screwed tight on the threaded portion 60 of the part 50, it deforms the limbs of the part 50 elastically, thereby pinching and clamping strands of the ligature 14 between the rod 18 and the inside wall(s) of the recess 58, in a manner explained below.

Figure 6A:
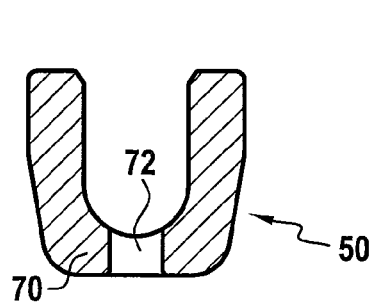
FIG. 6A is a section view on line AA of FIG. 6.
Figure 6:
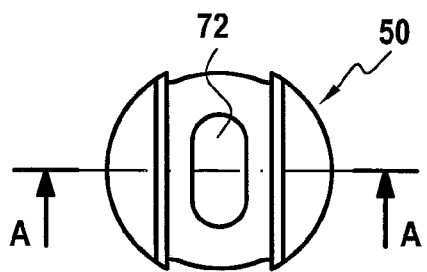
FIG. 6 is a plan view of a portion of the FIG. 1 connection device.

As shown better in FIGS. 6 and 6A, the part 50 includes in its bottom 70 a passage 72 for passing the ligature 14 in a manner explained below.

Figure 7:
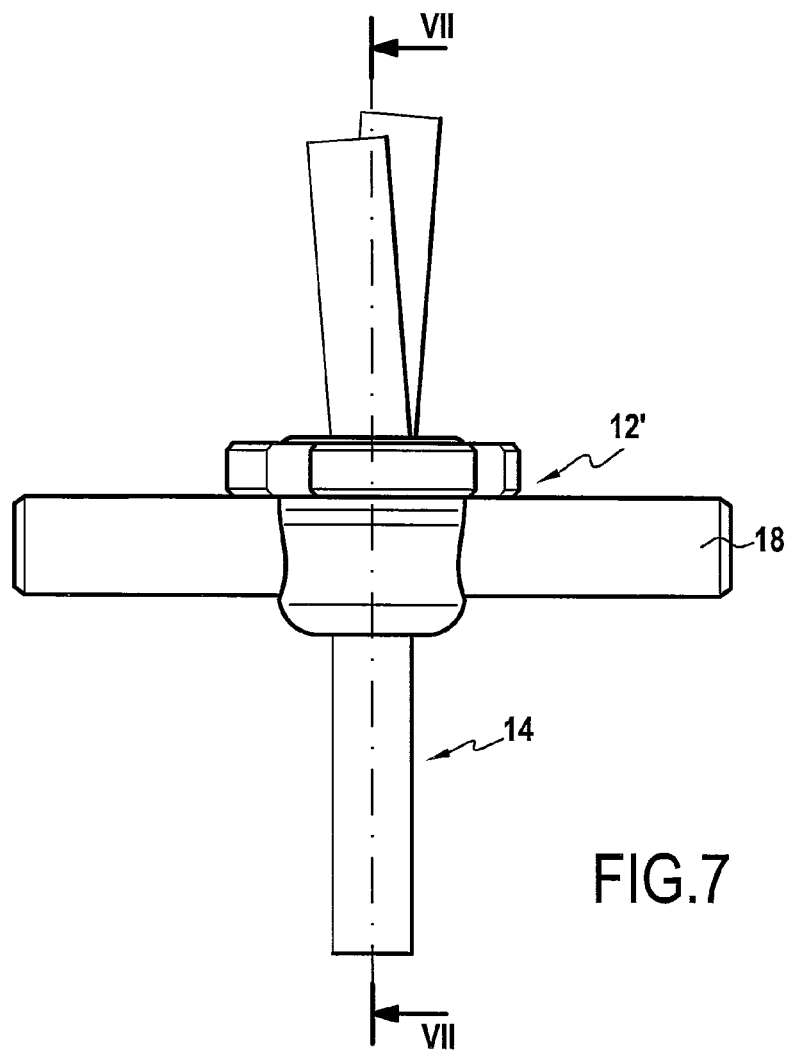
FIG. 7 is a face view of the fixing system of the second embodiment.
Figure 7A:
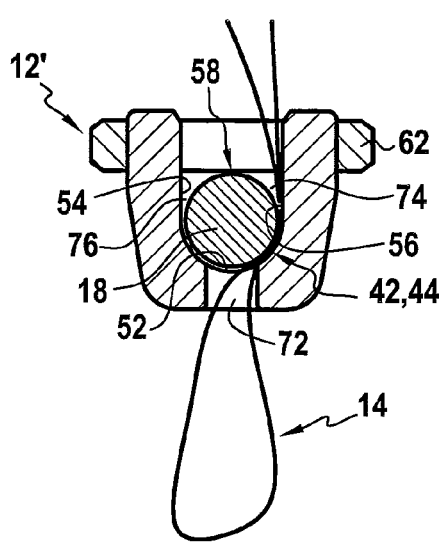
FIGS. 7A and 7B are section views on line VII-VII of FIG. 7 showing two ways in which the flexible ligature can be put into place.
Figure 7B:
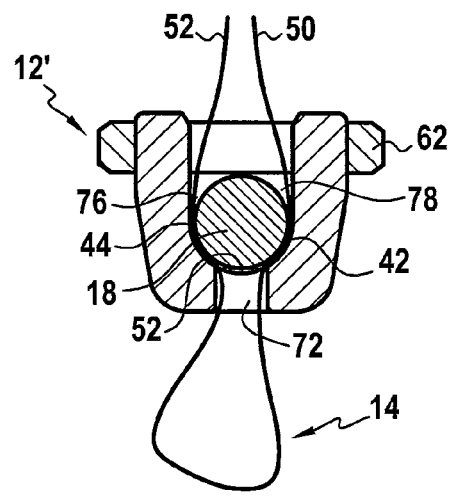

With reference to FIGS. 7, 7A, and 7B, there follows a description of two different ways of putting the flexible ligature 14 into place inside the connecting part 12' in the second embodiment. The side wall of the rod 18 and the inside wall of the recess 58 of the part 50 potentially define two passageways 74 and 76 for passing the middle strands of the flexible ligature 14. In the configuration shown in FIG. 7A, only the passageway 74 is used. Thus, both intermediate strands 42 and 44 of the flexible ligature 14 are disposed in the passage 74. This disposition presents all of the advantages described with reference to the first embodiment.

In the configuration shown in FIG. 7B, the middle strands 42 and 44 of the flexible ligature 14 are disposed respectively one in each of the passageways 76 and 78, i.e. on either side of the rod 18. This configuration likewise presents all of the advantages described with reference to the first embodiment of the device since the free ends 50 and 52 of the ligature 14 are accessible for exerting the desired traction in order to obtain suitable clamping on the spinous process prior to locking the clamping ring 62 on the part 52.

This second embodiment presents the advantage of being simpler in design since it serves in particular to avoid making two longitudinal parts constituting a kind of clamp hinged on the pin 24.

It will be understood that in both embodiments, the locking means are constituted by an element that is distinct from the connecting part and that is removable therefrom. In addition, in both cases, the locking means co-operate with the connecting part by screw engagement. It is thus possible to adjust accurately the dimensions of the ligature-passing passageway(s) as defined by the connecting part and the rod. In an initial stage, the coefficient of friction between the coefficient of the ligature and secondly the rod and the connecting part can be adjusted. In the final stage, very effective clamping of the ligature is obtained between the rod and the locking part.

What is claimed is:

1. A bone fixing system for engaging a bone, comprising:
   a connecting part comprising:
      a first opening;
      a second opening;
      a transverse passage sized to receive a rod therethrough; and
      a bore hole;
   a flexible ligature comprising:
      a first end portion extendable from the first opening of the connecting part in a first direction;
      a second end portion extendable from the first opening of the connecting part in the first direction with the first end portion; and
      a loop portion between the first end portion and the second end portion, the loop portion extendable from the second opening of the connecting part; and
   an adjustable locking member configured for engagement with the bore hole of the connecting part to lock the flexible ligature relative to the connecting part, wherein first and second portions of the flexible ligature are pressed directly against each other within the connecting part when the ligature is locked relative to the connecting part.

2. A bone fixing system according to claim 1, wherein the connecting part is configured to be secured to a rod extending through the transverse passage, such that the rod presses directly against one of the first and second portions of the flexible ligature thereby locking the first and second portions of the flexible ligature between the rod and an inner wall of the connecting part.

3. A bone fixing system according to claim 1, wherein the loop portion of the flexible ligature is sized to pass around a bony element.

4. A bone fixing system according to claim 1, wherein the first opening of the connecting part and the second opening of the connecting part are positioned on opposite sides of the connecting part.

5. A bone fixing system according to claim 1, wherein the adjustable locking member is configured to engage with the bore hole of the connecting part in a plurality of positions relative to the connecting part.

6. A bone fixing system according to claim 5, wherein the plurality of positions of the adjustable locking member relative to the connecting part comprises:
 a first position in which the flexible ligature is free to move within the first and second opening; and
 a second position in which the flexible ligature is prevented from moving in translation relative to the connecting part.

7. A bone fixing system according to claim 6, wherein the plurality of positions of the adjustable locking member relative to the connecting part further comprises intermediate positions between the first position and the second position in which a coefficient of friction is created between a portion of the flexible ligature and the connecting part.

8. A bone fixing system according to claim 1, wherein the first opening of the connecting part is positioned near the bore hole of the connecting part.

9. A bone fixing system according to claim 1, wherein the adjustable locking member cooperates with the connecting part by screw-fastening.

10. A bone fixing system according to claim 9, wherein the adjustable locking member comprises a screw.

11. A bone fixing system according to claim 10, wherein tightening the screw relative to the bore hole of the connecting part locks the flexible ligature in place.

12. A bone fixing system according to claim 11, wherein locking the flexible ligature in place prevents any additional portion of the flexible ligature from becoming part of the loop portion of the flexible ligature, thereby defining a size of the loop portion of the flexible ligature.

13. A method for engaging a bone, comprising:
 advancing a rod through a transverse passage of a connecting part;
 passing a portion of a flexible ligature through the connecting part to form a loop such that a first end portion of the flexible ligature and a second end portion of the flexible ligature both extend from a first opening of the connecting part in a first direction, first and second portions of the flexible ligature are pressed directly against each other within the connecting part, and the loop extends from a second opening of the connecting part; and
 engaging an adjustable locking member with a bore hole of the connecting part to provide controlled locking of the flexible ligature relative to the connecting part.

14. A method according to claim 13, further comprising securing the connecting part to the rod extending through the transverse passage of the connecting part such that the rod presses directly against one of the first and second portions of the flexible ligature.

15. A method according to claim 13, further comprising placing the portion of the flexible ligature around a bony element.

16. A method according to claim 15, further comprising extracting traction on the at least one end of the flexible ligature until sufficient tension is obtained in the portion of the flexible ligature placed around the bony element.

17. A method according to claim 16, further comprising tightening the adjustable locking member in the bore hole of the connecting part, locking of the flexible ligature relative to the connecting part.

18. A method according to claim 13, wherein the adjustable locking member comprises a screw and wherein engaging the adjustable locking member with the bore hole of the connecting part further comprises threading the screw relative to the bore hole of the connecting part.

19. A method according to claim 18, wherein tightening the screw causes the connecting part to create a force against the flexible ligature.

20. A method according to claim 19, wherein the force against the flexible ligature prevents any additional portion of the flexible ligature from becoming part of the loop, thereby defining a size of the loop.

\* \* \* \* \*